US012620774B2

(12) United States Patent
Saito et al.

(10) Patent No.: US 12,620,774 B2
(45) Date of Patent: May 5, 2026

(54) ANALYSIS DEVICE

(71) Applicant: KABUSHIKI KAISHA TOSHIBA,
Tokyo (JP)

(72) Inventors: Shinji Saito, Yokohama (JP); Yoichiro Kurita, Minato (JP); Rei Hashimoto, Edogawa (JP); Kei Kaneko, Yokohama (JP); Takayoshi Fujii, Yokohama (JP)

(73) Assignee: KABUSHIKI KAISHA TOSHIBA,
Tokyo (JP)

( * ) Notice: Subject to any disclaimer, the term of this patent is extended or adjusted under 35 U.S.C. 154(b) by 1085 days.

(21) Appl. No.: 17/651,094

(22) Filed: Feb. 15, 2022

(65) Prior Publication Data

US 2023/0063072 A1     Mar. 2, 2023

(30) Foreign Application Priority Data

Aug. 27, 2021     (JP) ................................. 2021-139049

(51) Int. Cl.
*H01S 5/026* (2006.01)
*A61B 5/145* (2006.01)
(Continued)

(52) U.S. Cl.
CPC ........ *H01S 5/0262* (2013.01); *A61B 5/14532* (2013.01); *A61B 5/1455* (2013.01);
(Continued)

(58) Field of Classification Search
CPC .... H01S 5/0262; H01S 5/0264; H01S 5/4087; H01S 5/42; A61B 5/14532; A61B 5/1455; A61B 2562/0238
See application file for complete search history.

(56) References Cited

U.S. PATENT DOCUMENTS 10,615,575 B2 *   4/2020   Liang .................. H01S 5/06236
10,718,491 B1 *   7/2020   Raring ................ H04B 10/116
(Continued)

FOREIGN PATENT DOCUMENTS

JP          2004-340797 A     12/2004
JP          2005-73763 A      3/2005
(Continued)

OTHER PUBLICATIONS

Gangyi Xu; Virginie Moreau; Yannick Chassagneux; Adel Bousseksou; Raffaele Colombelli; G. Patriarche; G. Beaudoin; I. Sagnes, Surface-emitting quantum cascade lasers with metallic photonic-crystal resonators, 2009, Applied Physics Letters 94, 221101 to 221101-3 (Year: 2009).*

(Continued)

*Primary Examiner* — Sean P Dougherty
(74) *Attorney, Agent, or Firm* — Oblon, McClelland, Maier & Neustadt, L.L.P.

(57)          ABSTRACT

An analysis device includes a substrate including a first surface, and a second surface positioned at a side opposite to the first surface; a light source part located at the first surface of the substrate, the light source part including a quantum cascade laser; a light detector located at the first surface of the substrate; and a wiring part located at the first surface of the substrate, the wiring part being electrically connected with the light source part and the light detector.

11 Claims, 5 Drawing Sheets

(51) Int. Cl.

| | |
|---|---|
| *A61B 5/1455* | (2006.01) |
| *H01S 5/11* | (2021.01) |
| *H01S 5/183* | (2006.01) |
| *H01S 5/34* | (2006.01) |
| *H01S 5/42* | (2006.01) |

(52) U.S. Cl.
CPC ............ *H01S 5/11* (2021.01); *H01S 5/18305* (2013.01); *H01S 5/3402* (2013.01); *H01S 5/423* (2013.01); *A61B 2562/0238* (2013.01)

(56) References Cited

U.S. PATENT DOCUMENTS

| | | | |
|---|---|---|---|
| 2003/0021327 A1 | 1/2003 | Murry | |
| 2015/0112170 A1* | 4/2015 | Amerson, III | A61B 5/14532 600/316 |
| 2017/0115213 A1* | 4/2017 | Ito | H01S 5/0264 |
| 2018/0000386 A1 | 1/2018 | Yamakawa | |
| 2019/0074663 A1 | 3/2019 | Saito et al. | |
| 2020/0408686 A1 | 12/2020 | Ogawa | |
| 2022/0042672 A1* | 2/2022 | Raring | H01S 5/4087 |
| 2022/0057319 A1 | 2/2022 | Saito et al. | |

FOREIGN PATENT DOCUMENTS

| | | | |
|---|---|---|---|
| JP | 2005-91240 A | 4/2005 | |
| JP | 2014-82273 A | 5/2014 | |
| JP | 2015-45629 A | 3/2015 | |
| JP | 2016-102770 A | 6/2016 | |
| JP | 2017-147428 A | 8/2017 | |
| JP | 2019-91838 A | 6/2019 | |
| JP | WO 2019/176157 A1 | 9/2019 | |
| JP | 2019-197933 A | 11/2019 | |
| JP | 2021-37321 A | 3/2021 | |
| JP | 2022-34791 A | 3/2022 | |
| WO | WO-2022059260 A1 * | 3/2022 | ......... H10F 77/1248 |

OTHER PUBLICATIONS

Benedikt Schwarz, Peter Reininger, Daniela Ristanic, Hermann Detz, Aaron Maxwell Andrews, Werner Schrenkl & Gottfried Strasse, Monolithically integrated mid-infrared lab-on-a-chip using plasmonics and quantum cascade structures, 2014, Nature Communications, 1-7 (Year: 2014).*

Japanese Office Action Issued Jan. 28, 2025 in Japanese Patent Application No. 2021-139049 (with unedited computer-generated English translation), 8 pages.

Japanese Office Action issued Oct. 10, 2024 in Japanese Patent Application No. 2021-139049 (with unedited computer-generated English translation) 6 pages.

* cited by examiner

ANALYSIS DEVICE

CROSS-REFERENCE TO RELATED APPLICATION

This application is based upon and claims the benefit of priority from Japanese Patent Application No. 2021-139049, filed on Aug. 27, 2021; the entire contents of which are incorporated herein by reference.

FIELD

Embodiments described herein relate generally to an analysis device.

BACKGROUND

Noninvasive techniques that are used to measure blood substance concentration include optical techniques. When using the mid-infrared wavelength region as in an embodiment of the invention, a higher light source output is required to measure a blood concentration in a blood vessel than to measure a concentration in the tissue fluid of a somatic cell, making it difficult to downsize the light source.

DETAILED DESCRIPTION

Figure 1:
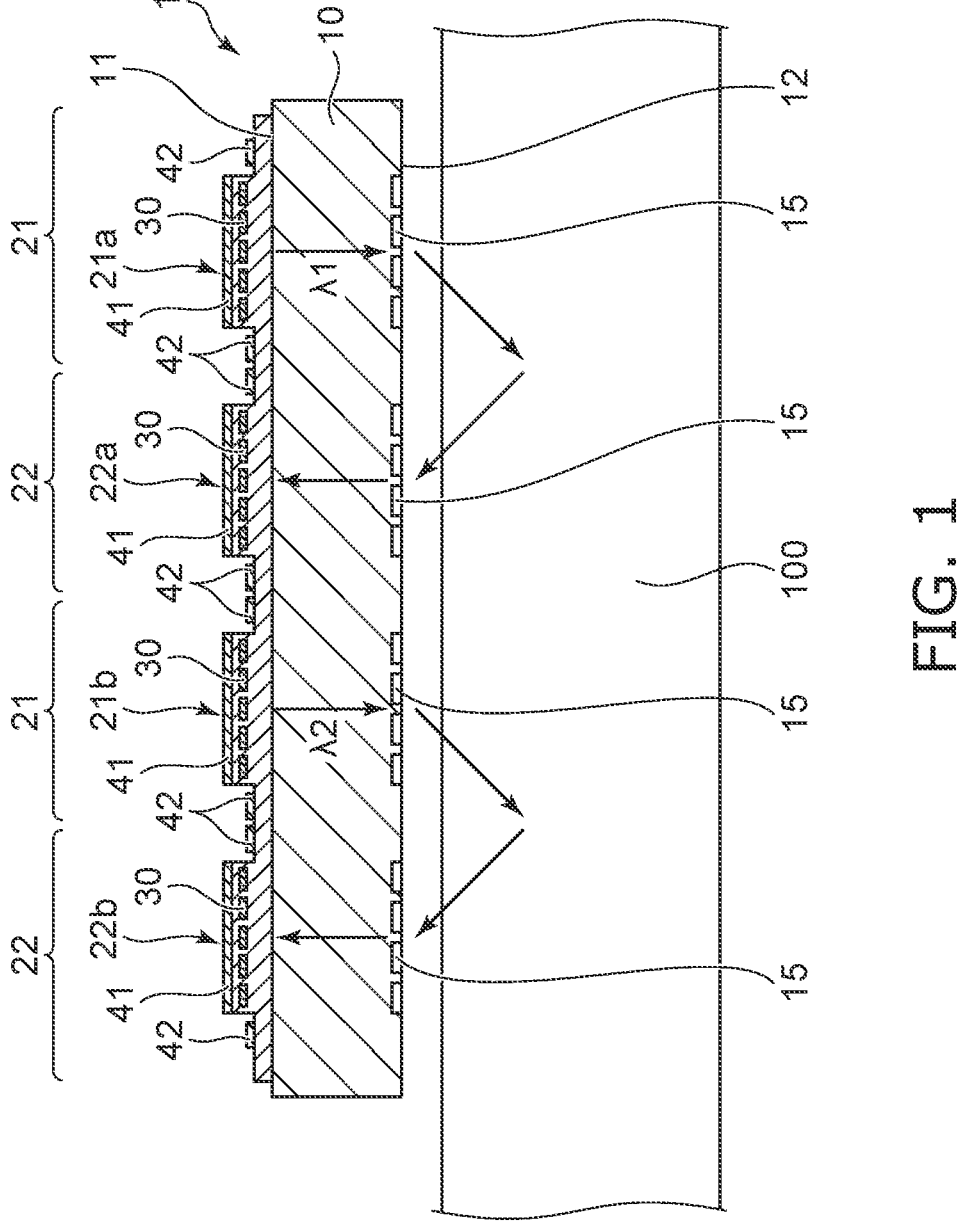
FIG. 1 is a schematic cross-sectional view of an analysis device of a first embodiment.

According to one embodiment, an analysis device includes a substrate including a first surface, and a second surface positioned at a side opposite to the first surface; a light source part located at the first surface of the substrate, the light source part including a quantum cascade laser; a light detector located at the first surface of the substrate; and a wiring part located at the first surface of the substrate, the wiring part being electrically connected with the light source part and the light detector.

Embodiments will now be described with reference to drawings. The same components in the drawings are marked with the same reference numerals.

First Embodiment

FIG. 1 is a schematic cross-sectional view of an analysis device 1 of a first embodiment.

The analysis device 1 includes a substrate 10, a light source part 21, and a light detector 22.

The substrate 10 is transmissive to light emitted by the light source part 21. The substrate 10 is, for example, a silicon substrate that includes Si. Or, the substrate 10 may be a compound semiconductor substrate that includes InP or GaAs. The substrate 10 includes a first surface 11 at which the light source part 21 and the light detector 22 are located, and a second surface 12 positioned at the side opposite to the first surface 11. The substrate 10 includes a lens portion 15 at the second surface 12. The lens portion 15 includes a recess, a protrusion, or a periodic structure obtained by patterning the substrate 10.

The light source part 21 includes a first quantum cascade laser 21a and a second quantum cascade laser 21b that have different oscillation wavelengths. The first quantum cascade laser 21a and the second quantum cascade laser 21b include, for example, light-emitting layers that include Group III-V compound semiconductors. The light-emitting layers each include a quantum well structure that generates intersubband transitions of carriers; and the light-emitting layers emit light due to intersubband transitions of electrons.

The first quantum cascade laser 21a and the second quantum cascade laser 21b each are surface-emitting and include a photonic crystal layer 30. The surface of the light-emitting layer is parallel to the first surface 11 of the substrate 10. The photonic crystal layer 30 includes a two-dimensional diffraction grating. As the two-dimensional diffraction grating, the photonic crystal layer 30 includes, for example, multiple pits arranged periodically in a plane parallel to the first surface 11 of the substrate 10. The light that is emitted by the light-emitting layer resonates due to the photonic crystal layer 30 in directions along the surface of the light-emitting layer and is emitted in a direction that is substantially perpendicular to the first surface 11 of the substrate 10. The substantially perpendicular direction also includes directions tilted in a range that is not less than 2° and not more than 10° with respect to the direction perpendicular to the first surface 11. This surface-emitting structure makes it easy to obtain a high output by increasing the element area. A photonic crystal can be used to realize a surface-emitting quantum cascade laser because the quantum cascade laser generates TM-polarized light. Furthermore, in principle, a quantum cascade laser is capable of high-speed operation and can generate extremely short pulses. The total energy can be reduced; pulses that have high peak values can be irradiated without damaging biological tissue; and the target detection substance inside the blood vessel can be measured with high sensitivity.

The light detector 22 includes a first quantum cascade detector 22a and a second quantum cascade detector 22b. The first quantum cascade detector 22a can detect the light emitted by the first quantum cascade laser 21a. The second quantum cascade detector 22b can detect the light emitted by the second quantum cascade laser 21b. The first quantum cascade detector 22a and the second quantum cascade detector 22b each are light detection elements that utilize intersubband transitions of electrons. When light that is incident along a direction perpendicular to the substrate is detected in a conventional quantum cascade detector, the thickness of the active region that absorbs the light and converts the light into electrons is at most about 2 μm; therefore, the absorption of the light is insufficient, and the sensitivity is extremely low. On the other hand, in the quantum cascade detector that uses the photonic crystal according to one embodiment of the invention, the sensitivity is high because the light that is perpendicularly incident on the substrate is converted into a direction parallel to the active layer by the photonic crystal and is sufficiently absorbed inside the active layer.

For example, the first quantum cascade detector 22a and the second quantum cascade detector 22b include the same type of semiconductor layers as the first and second quantum cascade lasers 21a and 21b. For example, the first quantum cascade laser 21a, the second quantum cascade laser 21b, the first quantum cascade detector 22a, and the second quantum cascade detector 22b are integrated on a growth substrate other than the substrate 10 and are subsequently bonded to the first surface 11 of the substrate 10 directly or via a silicon oxide film. Or, the first quantum cascade laser 21a, the second quantum cascade laser 21b, the first quantum cascade detector 22a, and the second quantum cascade detector 22b may be grown on the first surface 11 of the substrate 10.

Similarly to the first and second quantum cascade lasers 21a and 21b, for example, the first quantum cascade detector 22a and the second quantum cascade detector 22b are surface-receiving and include the photonic crystal layers 30.

The first quantum cascade laser 21a, the second quantum cascade laser 21b, the first quantum cascade detector 22a, and the second quantum cascade detector 22b each include a first electrode 41 and a second electrode 42.

Figure 2A:
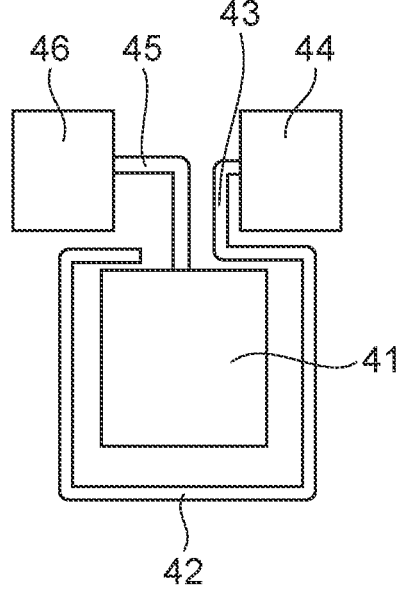
FIG. 2A and FIG. 2B are schematic top views of an electrode and a wiring part of the first embodiment.

The first electrode 41 is located above the photonic crystal layer 30. As shown in FIG. 2A, the second electrode 42 is located at the periphery of the first electrode 41 when viewed in top-view.

The analysis device 1 further includes a wiring part that is located at the first surface 11 of the substrate 10 and is electrically connected with the light source part 21 and the light detector 22. For example, Ti/Au, Ni/Au, AuGe/Au, etc., can be used as the material of the wiring part. As shown in FIG. 2A, the wiring part includes first wiring 45 that is connected with the first electrode 41, a first pad 46 that is connected with the first wiring 45, second wiring 43 that is connected with the second electrode 42, and a second pad 44 that is connected with the second wiring 43. The light source part 21 and the light detector 22 are electrically connected with an external circuit via wires bonded to the first and second pads 46 and 44.

Figure 2B:
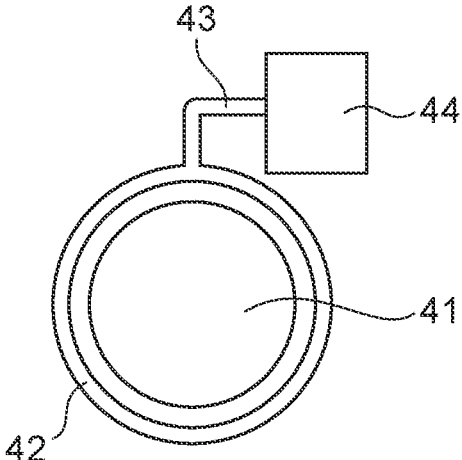

As shown in FIG. 2B, the first electrode 41 may be circular when viewed in top-view. The second electrode 42 surrounds the first electrode 41 in a ring shape when viewed in top-view. A wire may be directly bonded to the first electrode 41 without connecting the first electrode 41 to a pad.

The first quantum cascade laser 21a and the second quantum cascade laser 21b output laser light in the mid-infrared region. The first quantum cascade laser 21a outputs laser light of a wavelength λ1; and the second quantum cascade laser 21b outputs laser light of a wavelength λ2 that is different from λ1. λ1 and λ2 are, for example, not less than 7.8 μm and not more than 8.8 μm.

The laser light from the first and second quantum cascade lasers 21a and 21b travels through the substrate 10 toward the second surface 12 and is emitted outside the substrate 10 from the second surface 12. The lens portion 15 of the second surface 12 condenses or changes the direction of the laser light; and the laser light is, for example, incident on the skin of a human, reaches a blood vessel 100, and is reflected.

The laser light enters the substrate 10 through the second surface 12; and the lens portion 15 condenses or changes the direction of the laser light reflected by the blood vessel 100. The reflected light that enters the substrate 10 passes through the first surface 11 and is incident on the first and second quantum cascade detectors 22a and 22b. The light that is incident on the first and second quantum cascade detectors 22a and 22b undergoes photoelectric conversion. The intensity of the reflected light that corresponds to the glucose absorptance inside the blood vessel 100 is measured based on the electrical signal from the photoelectric conversion. Here, the blood glucose level is the concentration of glucose included in the blood. Accordingly, the blood glucose level can be determined based on the intensity of the reflected light that corresponds to the glucose absorptance in the blood vessel 100.

According to the embodiment, the light source part 21, the light detector 22, and the wiring part are integrated on the first surface 11 of the substrate 10 by using semiconductor processes. Also, the lens portion 15 is formed in the second surface 12 of the substrate 10 by patterning the substrate 10. Therefore, a compact noninvasive analysis device can be provided. For example, an analysis device that has a chip size of about 1 mm can be mounted in a portable terminal, etc.

The light source part 21 may include one quantum cascade laser; and the light detector 22 may include one quantum cascade detector. In such a case, the analysis device 1 can be further downsized. By using the two quantum cascade lasers 21a and 21b and the two quantum cascade detectors 22a and 22b, the blood glucose level can be determined with high accuracy based on the ratio of the glucose absorbance for light of two different wavelengths.

Second Embodiment

Figure 3:
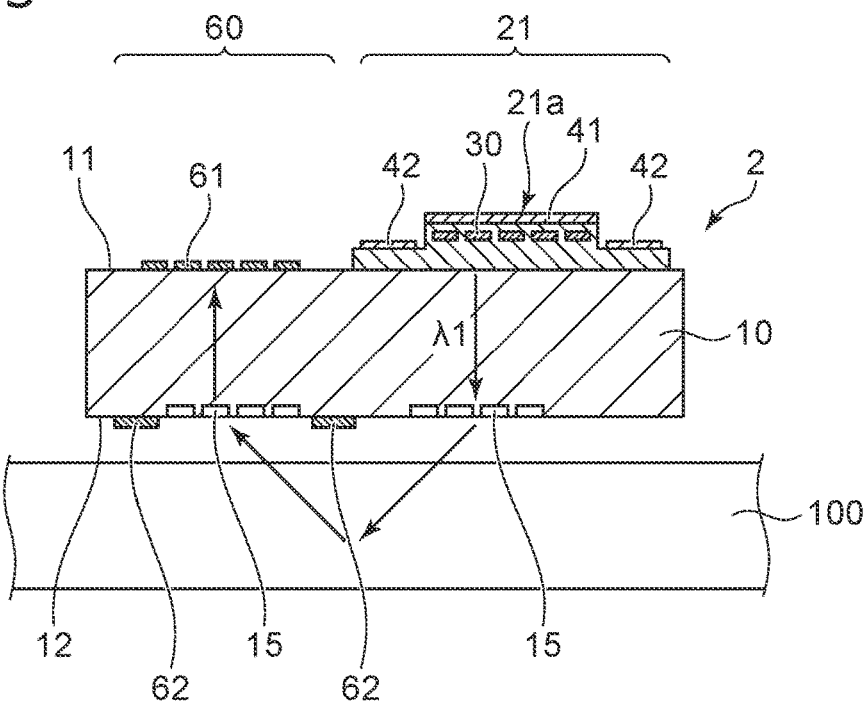
FIG. 3 is a schematic cross-sectional view of an analysis device of a second embodiment.

FIG. 3 is a schematic cross-sectional view of an analysis device 2 of a second embodiment.

Figure 4A:
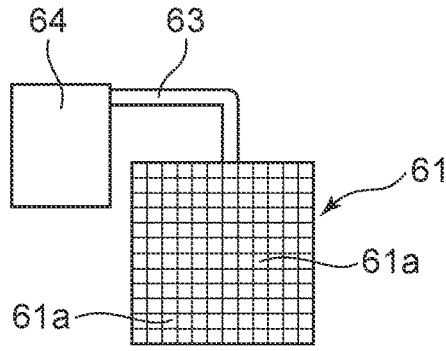
FIG. 4A is a schematic top view of a light detector of the second embodiment.

The analysis device 2 of the second embodiment includes a light detector 60 that utilizes plasmons. The light detector 60 includes a metal antenna 61 located at the first surface 11 of the substrate 10. As shown in FIG. 4A, the metal antenna 61 includes, for example, multiple metal pillars (or an uneven structure) 61a that form a nanostructure body. A wiring part that is electrically connected with the metal antenna 61 is located at the first surface 11. The wiring part includes wiring 63 that is connected with the metal antenna 61, and a pad 64 that is connected with the wiring 63.

Figure 4B:
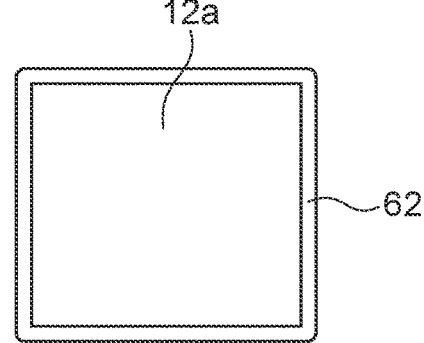
FIG. 4B is a schematic bottom view of the light detector of the second embodiment.

A back electrode 62 is located at the second surface 12 of the substrate 10. As shown in FIG. 4B, the back electrode 62 surrounds a light incident region 12a of the second surface 12. The lens portion 15 is located at the light incident region 12a.

In the second embodiment as well, a compact noninvasive analysis device can be provided because the light source part 21, the metal antenna 61, and the wiring part are integrated on the first surface 11 of the substrate 10 by using semiconductor processes.

Third Embodiment

Figure 5:
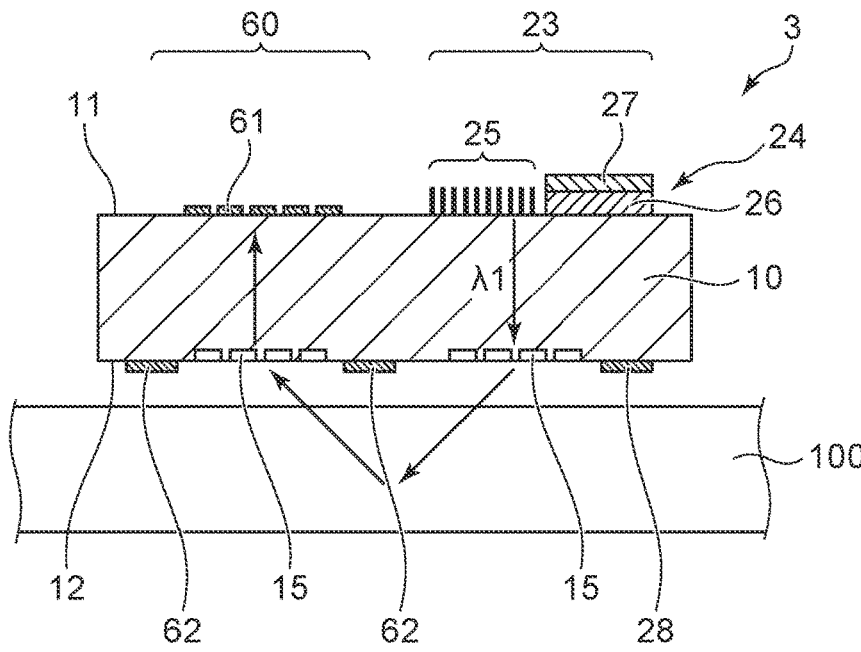
FIG. 5 is a schematic cross-sectional view of an analysis device of a third embodiment.

FIG. 5 is a schematic cross-sectional view of an analysis device 3 of a third embodiment.

The analysis device 3 of the third embodiment includes an edge-emitting quantum cascade laser 24 and a diffraction grating 25 as a light source part 23.

Figure 6A:
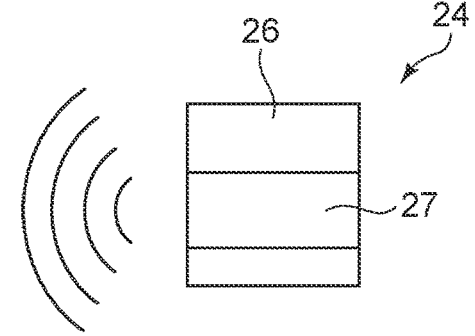
FIG. 6A is a schematic top view of a quantum cascade laser of the third embodiment.
Figure 6B:
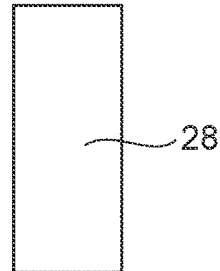
FIG. 6B is a schematic bottom view of a lower surface electrode of the third embodiment.

FIG. 6A is a schematic top view of the quantum cascade laser 24; and FIG. 6B is a schematic bottom view of a lower surface electrode 28 of the quantum cascade laser 24.

The quantum cascade laser 24 includes, for example, a semiconductor layer 26 that includes a Group III-V compound semiconductor, an upper surface electrode 27 that is located on the semiconductor layer 26, and the lower surface electrode 28 located at a region of the second surface 12 of the substrate 10 below the semiconductor layer 26.

The diffraction grating 25 is located at the first surface 11 of the substrate 10 and is positioned at the side of the end surface (the light-emitting surface) of the quantum cascade laser 24. The lens portion 15 is positioned at a region of the second surface 12 below the diffraction grating 25. The travel direction of the laser light emitted from the end surface of the quantum cascade laser 24 is changed by the diffraction grating 25 to the direction from the first surface 11 toward the second surface 12.

The diffraction efficiency of a surface-emitting quantum cascade laser that includes a photonic crystal layer is greater than that of the combination of an edge-emitting quantum cascade laser and a diffraction grating.

Fourth Embodiment

Figure 7:
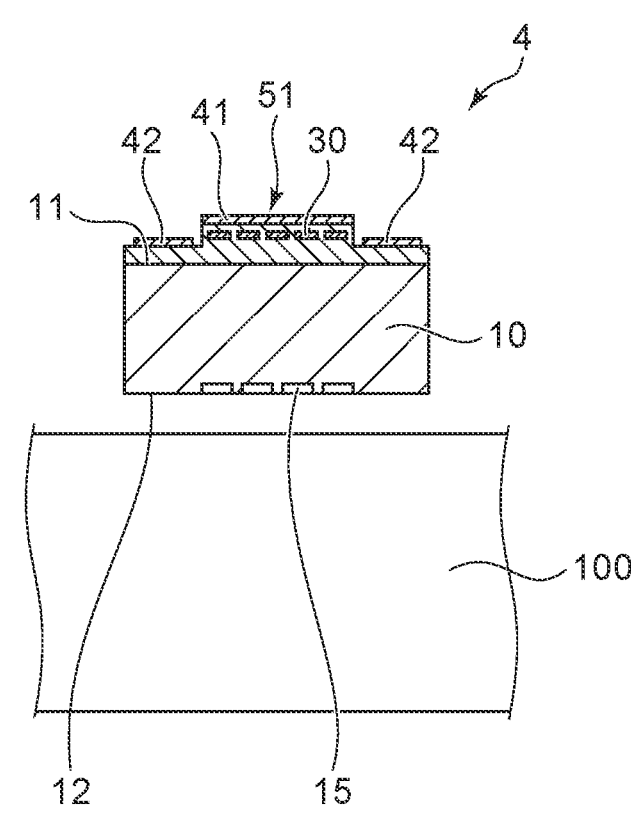
FIG. 7 is a schematic cross-sectional view of an analysis device of a fourth embodiment.

FIG. 7 is a schematic cross-sectional view of an analysis device 4 of a fourth embodiment.

The analysis device 4 of the fourth embodiment includes a quantum cascade element 51 that is used as both a light source part and a light detector. The quantum cascade element 51 is surface-emitting/receiving and includes the photonic crystal layer 30.

The quantum cascade element 51 includes a surface-emitting mode of emitting laser light in the direction from the first surface 11 toward the second surface 12 of the substrate 10, and a surface-receiving mode of receiving the reflected light that enters through the second surface 12 and is received at the first surface 11 side. The one quantum cascade element 51 can be used as both the light source part and the light detector by high-speed switching between the surface-emitting mode and the surface-receiving mode. According to such a fourth embodiment, the analysis device 4 can be further downsized.

The analysis devices of the embodiments described above also can be used to noninvasively acquire biological information other than the blood glucose level.

Although the quantum cascade laser that is the light source and the quantum cascade detector are described above in detail, the drive circuit of the quantum cascade laser and the electrical circuit that processes the electrical signal from the quantum cascade detector may be formed on the substrate. Such a configuration makes a more compact device possible.

A general structure or configuration that can produce this wavelength region may be used as the structures of the quantum cascade laser and the quantum cascade detector.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modification as would fall within the scope and spirit of the inventions.

What is claimed is:

1. An analysis device, comprising:
a substrate including
a first surface, and
a second surface positioned at a side opposite to the first surface;
a light source part located at the first surface of the substrate, the light source part including a quantum cascade laser;
a light detector located at the first surface of the substrate; and
a wiring part located at the first surface of the substrate, the wiring part being electrically connected with the light source part and the light detector,
wherein the substrate is transmissive to a laser light emitted by the quantum cascade laser,
a laser light emitted by the quantum cascade laser travels through the substrate toward the second surface and is emitted outside the substrate from the second surface, and
the light detector receives a reflected light of the laser light incident on the second surface of the substrate from the outside.

2. The device according to claim 1, wherein the quantum cascade laser is surface-emitting and includes a photonic crystal layer.

3. The device according to claim 1, wherein the light detector includes a quantum cascade detector.

4. The device according to claim 1, wherein the light detector includes a metal antenna.

5. The device according to claim 1, wherein
the light source part includes a first quantum cascade laser and a second quantum cascade laser, and
the first quantum cascade laser and the second quantum cascade laser have different oscillation wavelengths.

6. The device according to claim 1, wherein the substrate includes Si, InP, or GaAs.

7. The device according to claim 1, wherein the substrate includes a lens portion at the second surface.

8. An analysis device, comprising:
a substrate including
a first surface, and
a second surface positioned at a side opposite to the first surface;
a quantum cascade element located at the first surface of the substrate, the quantum cascade element being used as a light source part and a light detector; and
a wiring part located at the first surface of the substrate, the wiring part being electrically connected with the quantum cascade element,
wherein the substrate is transmissive to a laser light emitted by the quantum cascade element,
a laser light emitted by the quantum cascade element travels through the substrate toward the second surface and is emitted outside the substrate from the second surface, and
the quantum cascade element receives a reflected light of the laser light incident on the second surface of the substrate from the outside.

9. The device according to claim 8, wherein the quantum cascade element is surface-emitting/receiving and includes a photonic crystal layer.

10. The device according to claim 8, wherein the substrate includes Si, InP, or GaAs.

11. The device according to claim 8, wherein the substrate includes a lens portion at the second surface.

* * * * *